United States Patent
Barbier et al.

(10) Patent No.: US 6,756,364 B2
(45) Date of Patent: Jun. 29, 2004

(54) METHOD OF REDUCING GASTROINTESTINAL SIDE EFFECTS ASSOCIATED WITH ORLISTAT TREATMENT

(75) Inventors: Pierre Barbier, Rixheim (FR); Paul Hadvary, Biel-Benken (CH); Hans Lengsfeld, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/912,957

(22) Filed: Jul. 25, 2001

(65) Prior Publication Data

US 2002/0035089 A1 Mar. 21, 2002

(30) Foreign Application Priority Data

Jul. 28, 2000 (EP) .............................................. 00116393

(51) Int. Cl.[7] .............................................. A61K 31/70
(52) U.S. Cl. ............................. 514/57; 424/439; 514/54; 514/56; 514/58; 514/169; 514/449
(58) Field of Search ............................. 424/439; 514/54, 514/56, 57, 58, 169, 449

(56) References Cited

U.S. PATENT DOCUMENTS

| 4,598,089 A | | 7/1986 | Hadvary et al. | |
| 5,447,953 A | * | 9/1995 | Isler et al. ................. | 514/449 |
| 5,643,874 A | | 7/1997 | Bremer et al. | |
| 5,883,109 A | * | 3/1999 | Gregg et al. ................ | 514/321 |
| 6,004,996 A | | 12/1999 | Shah et al. | |
| 6,358,522 B1 | * | 3/2002 | Hug et al. .................. | 424/441 |

FOREIGN PATENT DOCUMENTS

| WO | WO 99/34786 | 7/1999 |
| WO | WO 00/40569 | 7/2000 |

OTHER PUBLICATIONS

Mutoh et al, *J. Antibiot*, pp. 1369–1375 (1994).

* cited by examiner

*Primary Examiner*—Elli Peselev
(74) *Attorney, Agent, or Firm*—George W. Johnston; John P. Parise

(57) ABSTRACT

A pharmaceutical combination or composition containing a lipase inhibitor, preferably orlistat, and a bile acid sequestrant is useful for treating obesity.

1 Claim, No Drawings

METHOD OF REDUCING GASTROINTESTINAL SIDE EFFECTS ASSOCIATED WITH ORLISTAT TREATMENT

BACKGROUND OF THE INVENTION

1. Field

The present invention relates to pharmaceutical combinations, compositions and methods for treating obesity.

2. Description

Bile acids are synthesized in the liver and enter the bile as glycine and taurine conjugates. They are released in salt form in bile during digestion and act as detergents to solubilize and consequently aid in digestion of dietary fats. Following digestion, bile acid salts are mostly reabsorbed in the ileum, complexed with proteins, and returned to the liver through the hepatic portal vein. The small amount of bile acid salts which are not reabsorbed by active transport are excreted via the distal ileum and large intestine as a portion of fecal material. Reducing reabsorption of bile acids within the intestinal tract can lower levels of bile acid circulating in the enterohepatic system thereby potentially reducing emulsification in the upper intestinal tract of dietary fat and reducing intestinal absorption of fat soluble drugs. One method of reducing the amount of bile acids that are reabsorbed, is oral administration of compounds that sequester the bile acids within the intestinal tract and cannot themselves be absorbed.

Orlistat (also known as tetrahydrolipstatin and sold under the brand name XENICAL®) is a potent inhibitor of gastrointestinal lipases, i.e. lipases that are responsible for breaking down ingested fat (gastric lipase, carboxylester lipase, pancreatic lipase). As a consequence of this, unabsorbed fat is excreted in the feces. Pancreatic lipase is the key enzyme for the hydrolysis of dietary triglycerides. Triglycerides that have escaped hydrolysis are not absorbed in the intestine. Pharmacological studies with human patients demonstrate potent inhibition of fat absorption and medically relevant reduction of body weight was achieved using lipase inhibitors. However, in a subgroup of the patients, unpleasant gastrointestinal side effects such as oily spotting, fatty/oily stools, fecal urgency, increased defecation and fecal incontinence are observed. Accordingly, there is a need in the art for lipase inhibiting compositions that minimize or suppress the side effects caused by inhibitors of digestive lipases.

SUMMARY OF THE INVENTION

The subject invention provides a pharmaceutical composition which comprises a lipase inhibitor and a pharmaceutically acceptable bile acid sequestrant.

Preferably, the composition further comprises one or more pharmaceutically acceptable excipients, the lipase inhibitor is orlistat, and the pharmaceutically acceptable bile acid sequestrant is selected from the group consisting of cholestyramine, colestipol, colesevelam, colestimide, sevelamer, cellulose derivatives, dextran derivatives, starch, starch derivatives, and pharmaceutically acceptable salts thereof. Especially preferred bile acid sequestrants are cellulose derivatives and dextran derivatives, such as DEAE-cellulose, guanidinoethylcellulose, or DEAE-Sephadex. Favorable starches or starch derivatives are β-cyclodextrin, γ-cyclodextrin, retrograded starch, degraded starch, a combination of retrograded and degraded starch, hydrophobic starch, amylose, starch-diethylaminoethylether, and starch-2-hydroxyethylether.

Useful pharmaceutically acceptable excipients include fillers, surfactants, disintegrants, binders, lubricants, flowability enhancers, sweeteners, and colorants. A desirable composition comprises (a) from about 5 to about 1000 mg of a lipase inhibitor and (b) from about 0.1 to about 20 g of a bile acid sequestrant and favorably contains (a) from about 5 to about 1000 mg of a lipase inhibitor; (b) from about 0.1 to about 20 g bile acid sequestrant; (c) from about 0.1 to about 10 g of a filler; (d) from about 0.05 to about 3.0 g of a surfactant; (e) from about 0.05 to about 2.0 g of a disintegrant; (f) from about 0.02 to about 2.0 g of a binder; (g) from about 0.001 to about 1.0 g of a lubricant; (h) from about 0.1 to about 5.0 g of a flowability enhancer; (i) from about 0.01 to about 4.0 g of a sweetener; and (j) and about 0.001 to about 0.5 g of a colorant.

Preferred amounts of lipase inhibitor include from about 10 to about 500 mg, e.g. 120 mg, and 20 to about 100 mg, e.g. about 60 mg. Preferred amount of bile acid sequestrant are from about 0.5 to about 10 g and from about 1 to about 5 g.

Another aspect of the subject invention is a kit for use in the treatment of obesity, which comprises (a) a first component which is a lipase inhibitor and (b) a second component which is a bile acid sequestrant, present in oral unit dosage form.

A method of treating obesity in an obese patient is also provided. This method comprises administering to a patient in need of such treatment (a) a therapeutically effective amount of a lipase inhibitor and (b) a pharmaceutically acceptable bile acid sequestrant in an amount effective to reduce gastrointestinal side effects associated with the lipase inhibitor. The lipase inhibitor and bile acid sequestrant can be administered simultaneously, separately, and/or sequentially.

Further, the subject invention provides a method of reducing the gastrointestinal side effects associated with the lipase inhibitor treatment. This method comprises administering to a patient being treated with a lipase inhibitor an amount of a bile salt sequestrant effective to reduce the side effects associated with the lipase inhibitor treatment.

DETAILED DESCRIPTION OF THE PREFERRED EMBODIMENTS

The subject invention will now be described in terms of its preferred embodiments. These embodiments are set forth to aid in understanding the invention but are not to be construed as limiting.

The invention relates to a combination or composition comprising a lipase inhibitor, preferably a compound of formula I (orlistat), (I)

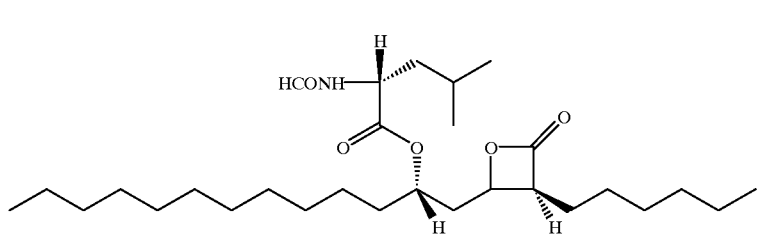

a pharmaceutically acceptable bile acid sequestrant and optionally one or more pharmaceutically acceptable excipient(s), e.g. a diluent or carrier. The present invention provides pharmaceutical combinations and compositions which are able to minimize or suppress the above mentioned side effects caused by inhibitors of digestive lipases. These compositions or combinations comprise a lipase inhibitor, preferably orlistat, a pharmaceutically acceptable bile acid sequestrant, optionally in conjunction with a pharmaceutically acceptable excipient, e.g. a diluent or carrier. The invention comprises also a method of treatment of obesity and associated comorbidities and other diseases treatable by lipase inhibitors which comprises administration of a therapeutically effective amount of a lipase inhibitor, preferably orlistat, and a therapeutically effective amount of a bile acid sequestrant.

It has been surprisingly found that pharmaceutically acceptable bile acid sequestrants, when ingested together with a lipase inhibitor, are able to suppress unpleasant gastrointestinal events. The reduction of unpleasant gastrointestinal side effects can improve the quality of life in sensitive patients during treatment with a lipase inhibitor and may further enhance compliance of the patients with drug intake and thus enhance the therapeutic benefit.

In more detail, the present invention relates to a pharmaceutical composition or combination comprising a lipase inhibitor, preferably a compound of formula I (orlistat) and a pharmaceutically acceptable bile acid sequestrant, optionally in conjunction with a pharmaceutically acceptable excipient, e.g. a diluent or carrier. The pharmaceutically acceptable bile acid sequestrant may be selected from the group consisting of cholestyramine, colestipol, diethylaminoethylcellulose (DEAE-cellulose), and starch derivatives like β-cyclodextrin and γ-cyclodextrin, more preferably from cholestyramine, colestipol, diethylaminoethylcellulose, β-cyclodextrin, and γ-cyclodextrin, and even more preferably from cholestyramine and colestipol, and most preferably the bile acid sequestrant is cholestyramine. The invention also provides the use of the above combination of compounds in the manufacture of a medicament for the treatment and prevention of obesity. Additionally, it provides the combination for use in the treatment and prevention of obesity.

Unless otherwise indicated the following definitions are set forth to illustrate and define the meaning and scope of the various terms used to describe the invention herein.

The term "pharmaceutically acceptable" as used herein means that the corresponding compounds are acceptable from a toxicity viewpoint.

The term "pharmaceutically acceptable salts" as used herein means salts of lipase inhibitors or bile acid sequestrants with inorganic or organic acids such as hydrochloric acid, hydrobromic acid, sulphuric acid, phosphoric acid, citric acid, formic acid, maleic acid, acetic acid, succinic acid, tartaric acid, methanesulphonic acid, p-toluenesulphonic acid and the like, which are non-toxic to living organisms. In the case of bile acid sequestrants having quaternary ammonium groups pharmaceutically acceptable salts mean correspondingly chlorides, bromides, sulphates, phosphates, citrates, formiates, maleates, acetates, succinates, tartrates, methanesulphonates, p-toluenesulphonates and the like.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. (All U.S. Patents mentioned herein are expressly incorporated by reference.) Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also encompasses pharmaceutically acceptable salts of these compounds. The term "lipase inhibitor" also refers to 2-oxy-4H-3,1-benzoxazin-4-ones which have been described in International Patent Application WO 00/40569 (Alizyme Therapeutics Ltd.), e.g. 2-decyloxy-6-methyl-4H-3,1-benzoxazin-4-one, 6-methyl-2-tetradecyloxy-4H-3,1-benzoxazin-4-one, and 2-hexadecyloxy-6-methyl-4H-3,1-benzoxazin-4-one. Most preferably, the term "lipase inhibitor" refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The term "bile acid sequestrant" refers to compound classes which are able to bind bile acids or bile acid salts by various principles, e.g. anion exchanging polymers containing amino groups, quaternary ammonium groups, etc. (amine containing polymers). In more detail the term refers to oligomers or polymers of different architecture (graft-, block-, multiblock-, homo-, copolymers), dendrimers, or hyperbranched structures containing either quaternary ammonium groups, substituted or unsubstituted pyridinium groups, substituted or unsubstituted primary, secondary, or tertiary alkyl- or arylamine groups, or any statistical or non-statistical combination thereof, which are capable of forming complexes with physiologically active bile acids and/or bile salts through non-covalent Van der Waals, hydrophobic and/or ionic interactions. For example, these structures can include, e.g., poly(amino acids) such as poly (lysine), poly(lactic acid-co-lysine) (PLAL), poly(vinyl amine), poly(allyl amine), poly(N-alkylvinyl amine), poly (N,N-dialkyl amine), poly(N-alkylallyl amine), poly (ethylene imine) and other mono- or disubstituted poly (amine)s. Further polymers include poly(vinyl pyridinyl), poly(amide enamines), PAMAM dendrimers, polymers containing azo-groups, poly(dialkyl siloxane)s, poly (phosphazene)s, poly(acrylate)s, poly(methacrylate)s, poly (styrene), poly(amides), poly(ethers), poly(esters). Suitable side-chains can include cationic or neutral groups, substituted and unsubstituted alkyl or aryl groups, saturated or unsaturated alkyl groups, amino acids or functional groups such as amine or ammonium moieties, for example (Uhrich et. al., Chem. Rev. 1999, 99, 3181–3198). In addition, naturally occurring and subsequently synthetically modified polymers such as poly(amino saccharide)s (chitosan) or cellulose derivatives (e.g. diethylaminoethylcellulose, guanidinoethylcellulose) are also of particular interest. A further important class of bile acid sequestrants are compounds capable of forming host-guest inclusion complexes, such as β and γ-cyclodextrines.

Bile acid sequestrants and methods for their preparation have been described for example in International Patent Applications WO 95/34585 (Geltex Pharmaceuticals, Inc.; relating to polyamine salt hydrophobic sequestrants), WO94/27620 (Geltex Pharmaceuticals, Inc.; relating to the preparation of polymeric sequestrants for bile acids), and WO94/04596 (DuPont; relating to crosslinked polymeric ammonium salts).

For example, amine containing polymers, as defined herein, may comprise the compounds described in International Patent Application WO 94/27620. The polymers are characterized by a repeat unit having the formula

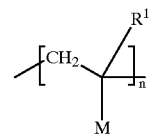

or copolymer thereof, where n is an integer; $R^1$ is H or an alkyl group (which may be straight chain or branched, substituted or unsubstituted, e.g., a $C_1$–$C_8$ alkyl, such as methyl); M is —C(O)—$R^2$ or —Z—$R^2$; Z is O, $NR^3$, S, or $(CH_2)_m$; m=0–10; $R^3$ is H or an alkyl group (which may be straight chain or branched, substituted or unsubstituted, e.g., $C_1$–$C_8$ alkyl, such as methyl); and $R^2$ is

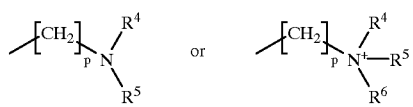

where p=0–10, and each $R^4$, $R^5$, and $R^6$, independently, is H, an alkyl group (which may be straight chain or branched, substituted or unsubstituted, e.g., $C_1$–$C_8$ alkyl, such as methyl), or an aryl group (e.g., having one or more rings and which may be substituted or unsubstituted, e.g., phenyl, naphthyl, imidazolyl, or pyridyl). In preferred embodiments, the polymer is crosslinked by means of a multifunctional crosslinking co-monomer, the co-monomer being present in an amount from about 0.5–25% (more preferably about 2.5–20% (or about 1–10%)) by weight, based upon total monomer weight. The compositions are non-toxic and stable when ingested in therapeutically effective amounts. The preparation of these compounds is described in International Patent Application WO94/27620 (Geltex Pharmaceuticals Inc.).

The term "bile acid sequestrants" also refer to compounds obtainable by molecular imprinting. Molecular imprinting is based on template polymerization in which polymers are prepared in the presence of a template mol. to be imprinted. Resultant polymers record the shapes and chemical properties of the templates in their matrixes and exhibit specific binding characteristics to the template molecule. The most significant advantage of this technique is to provide a simple procedure for the preparation of synthetic polymers capable of molecular recognition: complementary sites for the target molecules which are expected to be specific binding sites can be constructed with the aid of molecular self-assembling and no complicated synthesis is necessary. Molecular imprinted polymers have been described and the effectiveness of molecular imprinted polymers have been demonstrated [Ansell et al., *Curr. Opin. Biotechnol*, 7(1): 89–94 (1996)]. Imprinted polymers have been used for the chromatographic separation of amino acids, sugars, drugs and nucleotides. Drugs have been measured using imprinted polymers as antibody substitutes in radioligand binding assays [Sheaet al., *Trends Polym. Sci.*, 2(5): 166–173 (1994)]; [Takeuchi et al., *Chromatography*, 18(2): 102–103 (1997)]; [Nicholls, J., *Molecular Recognition*, 11 (1–6): 79–82 (1988)]. The term "bile acid sequestrants" also comprises pharmaceutically acceptable salts of these compounds.

More preferably the invention refers to compositions or combinations wherein the pharmaceutically acceptable bile acid sequestrant is selected from the group consisting of cholestyramine, colestipol, colesevelam, colestimide, sevelamer, cellulose and dextran derivatives, starch and starch derivatives and pharmaceutically acceptable salts thereof.

Cholestyramine (Quantalan®, Bristol-Myers Squibb) is a known compound and described for example in U.S. Pat. No. 4,902,501 and the references cited therein. It is a strong cationic resin containing quaternary ammonium functional groups bonded to a polymeric styrene-divinylbenzene structure:

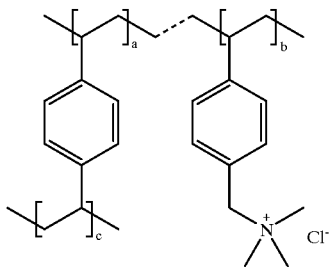

It was introduced in the therapy in 1959 and is prevailingly used in the management of the hypercholesterolemic states. The therapeutical activity of colestyramine is correlated to the capability of that resin of sequestering the biliary acids of the intestine, increasing up to 7–8 times the faecal elimination thereof. The use of cholestyramine resin as adjunctive therapy to diet in the management of patients with elevated cholesterol levels is noted in Remington's Pharmaceutical Sciences, 15th Ed. Mack Publishing Co. (1975) pp 733–734. Methods for the preparation of cholestyramine and appropriate compositions are known in the art (e.g. DE-A-38 08 191, EP-A-347 014, U.S. Pat. No. 5,695,749, U.S. Pat. No. 4,172,120 and EP-A-492 235).

Colestipol (Cholestabyl®, Pharmacia & Upjohn) is a known compound and described for example in U.S. Pat. Nos. 3,692,895, 3,803,237, and 5,807,582 and the references cited therein. It is a basic anion exchange resin described as a high molecular weight copolymer of diethylenetriamine and 1-chloro-2,3-epoxypropane (epichlorohydrin), with approximately one out of 5 amine nitrogens protonated, i.e. it is a copolymer of diethylenetriamine and epichlorohydrin with about 1 out of 5 amine nitrogens protonated:

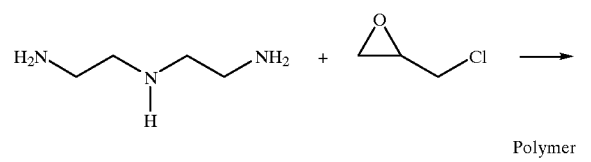

Polymer

It is a light yellow resin which is hygroscopic and swells when placed in water or aqueous fluids. See Merck Index (Tenth Edition) #2440, page 2438. Colestipol hydrochloride is commercially available in granule form as Colestid® Granules. See Physicians Desk Reference (PDR) 42nd Ed., p. 2119 (1988). Colestid® Granules are marketed as a hyperlipidemia agent for oral use. Colestipol binds bile acids in the intestine forming a complex that is excreted in the faeces. This nonsystemic action results in a partial removal of the bile acids from the enterohepatic circulation, preventing their reabsorption.

Colesevelam and colesevelam hydrochloride (Cholestagel® or WelChol®) are cholesterol-lowering agents [*Polym. Prepr.*, 41: 735–736 (2000)]. Colesevelam is a polyamine-copolymer of the three amines mentioned below, which are cross-linked with epichlorhydrine. Other names are 1-hexanaminium, N,N,N-trimethyl-6-(2-propenylamino)-, chloride, polymer with (chloromethyl) oxirane, 2-propen-1-amine and N-2-propenyl-1-decanamine, hydrochloride (9CI); or 1-Decanamine, N-2-propenyl-, polymer with (chloromethyl)oxirane, 2-propen-1-amine and N,N,N-trimethyl-6-(2-propenylamino)-1-hexanaminium chloride, hydrochloride (9CI); 2-Propen-1-amine, polymer with (chloromethyl)oxirane, N-2-propenyl-1-decanamine and N,N,N-trimethyl-6-(2-propenylamino)-1-hexanaminium chloride, hydrochloride (9CI); Oxirane, (chloromethyl)-, polymer with 2-propen-1-amine, N-2-propenyl-1-decanamine and N,N,N-trimethyl-6-(2-propenylamino)-1-hexanaminium chloride, hydrochloride (9CI); Cholestagel; Colesevelam hydrochloride; GT 31–104; or GT 31–104HB (see also Holmes-Farley, S. et al., *Polym. Prepr.* (*Am. Chem. Soc., Div. Polym. Chem.*), 41(1): 735–736 (2000)]. The three relevant amines have the formula

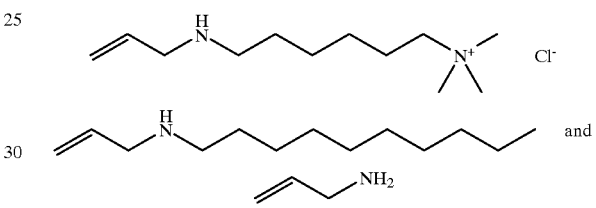

Epichlorohydrine has the following formula

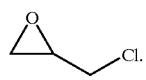

Colesevelam and colesevelam hydrochloride have been described in U.S. Pat. Nos. 5,607,669, 5,624,963, 5,679,717, 5,693,675, 5,917,007, and 5,919,832:

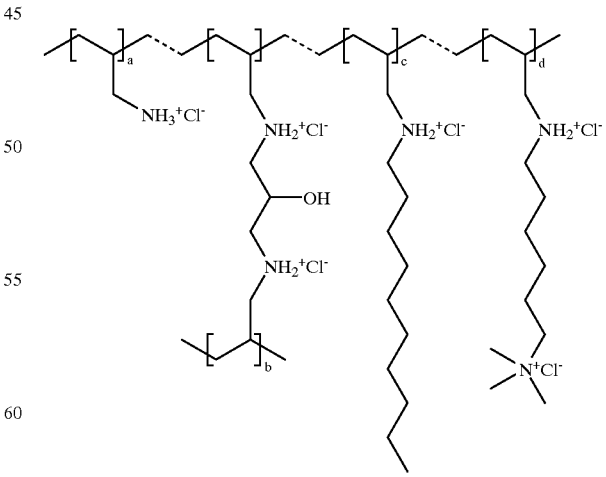

Sevelamer and its hydrochloride (Renagel®, GelTex) is a polymeric phosphate binder intended for oral administration. Sevelamer hydrochloride is poly(allylamine hydrochloride) crosslinked with epichlorohydrin in which forty percent of the amines are protonated:

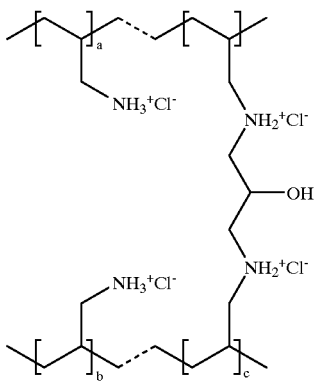

It is known chemically as poly(allylamine-co-N,N'-diallyl-1,3-diamino-2-hydroxypropane) hydrochloride. Sevelamer hydrochloride is hydrophilic, but insoluble in water. The compound, its preparation and use has been described in U.S. Pat. Nos. 5,496,545 and 5,667,775 and in International Patent Application WO95/05184.

Colestimide (Cholebine®; Mitsubishi-Tokoyo Pharmaceuticals) is a 2-methylimidazole polymer with 1-chloro-2,3-epoxypropane:

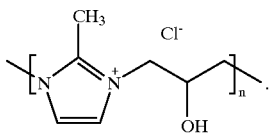

The binding of bile acids has been described e.g. in Mitsuka et al., *Japanese Pharmacology & Therapeutics*, 24(Suppl. 4): 103 (1996), Mitsuka et al., *Japanese Pharmacology & Therapeutics*, 24(Suppl. 4): 111 (1996) and Mitsuka et al., *Japanese Pharmacology & Therapeutics*, 24(Suppl. 4): 127 (1996).

Various cellulose and dextran anion exchangers bind bile acids in vitro under conditions of pH and ionic strength resembling those in the lumen of the small intestine [Parkinson, Thomas M., *J. Lipid Res.*, 8(1): 24–29 (1967)]; [Nichifor et al., *Pharma Sci.*, 4(6): 447–452 (1994)]. Of these substances, DEAE-cellulose, guanidinoethylcellulose, and DEAE-Sephadex reduce hypercholesterolemia when added to the diet of cholesterol-fed cockerels. In addition, DEAE-Sephadex reduced serum sterols in normocholesterolemic cockerels and dogs, lowered serum phospholipids and triglycerides in cholesterol-fed hypercholesterolemic cockerels and in normocholesterolemic dogs, and increased fecal excretion of bile acids in hypercholesterolemic cockerels. These insoluble cationic polymers evidently exert their hypocholesterolemic effects by interrupting the enterohepatic circulation of bile acids. DEAE-celulloses are compounds wherein diethylaminoethyl-groups are covalently bound to the cellulose hydroxylic groups. DEAE-celluloses are known substances and commercially available (e.g. Sigma-Aldrich). Guanidinoethylcelluloses are compounds wherein guanidinoethyl-groups are covalently bound to the cellulose hydroxylic groups. Guanidinoethylcelluloses are known substances and commercially availalbe. DEAE-Sephadex is a cross-linked dextran derivative wherein diethylaminoethyl-groups are covalently bound to dextran. DEAE-Sephadex compositions are commercially availalbe (e.g. Pharmacia Fince Chemicals). DEAE-cellulose, guanidinoethylcellulose and DEAE-Sephadex are especially useful as bile sequestrant agent, preferably DEAE-cellulose.

The term "starch and derivatives thereof" comprise compounds which are able to form inclusion complexes with free and conjugated bile salts and bile acids. Examples are β-, and γ-cyclodextrin, which contain, respectively, seven, and eight anhydroglucose ($C_6H_{10}O_5$) units. These molecules are doughnut-shaped rings having a hollow cavity of a specific volume. The polar hydroxyl groups are oriented to the outside of the rings, giving the outer surface a hydrophilic nature. In contrast, the internal cavity has a hydrophobic (lipophilic) nature. Because of this unique structure, cyclodextrins, as the "host" molecules, are able to hold "guest" molecules of suitable size (generally of a molecular weight between 80 and 250), shape, and hydrophobicity within their cavity. ("Production and Potential Food Applications of Cyclodextrins" Food Technology, January 1988, pp. 96–100). β-, and γ-cyclodextrin are commercially available compounds (e.g. Sigma-Aldrich). Other examples of starch and derivatives thereof are retrograded and/or degraded starch e.g. maltodextrin, hydrophobic starch, amylose, and starch derivatives, e.g. starch-diethylaminoethylether, starch-2-hydroxyethylether and the like ("Lexikon der Hilfsstoffe für Pharmazie, Kosmetik und angrenzende Gebiete", H. P. Fiedler, Editio Cantor Aulendorf, Bd. 2., 3. Auflage, 1989, pp. 1147–1154). Preferably starch derivatives are selected from the group consisting of consisting of β- or γ- cyclodextrin, retrograded and/or degraded starch, e.g. maltodextrin, hydrophobic starch, amylose, starch-diethylaminoethylether and starch-2-hydroxyethylether, preferably from β- or γ-cyclodextrin (Wacker Chemie; Gattfoseé).

In a preferred embodiment the bile acid sequestrant is a cellulose or dextran derivative, e.g. DEAE-cellulose, guanidinoethylcellulose, and DEAE-Sephadex, preferably DEAE-cellulose.

In another preferred embodiment of the present invention, the starch or starch derivative is selected from the group consisting of β- or γ-cyclodextrin, retrograded and/or degraded starch, hydrophobic starch, amylose, starch-diethylaminoethylether and starch-2-hydroxyethylether, preferably β- or γ-cyclodextrin.

In a further embodiment of the present invention, the bile acid sequestrant is selected from the group consisting of cholestyramine, colestipol, colesevelam, colestimide, sevelamer, cellulose, DEAE-cellulose, guanidinoethylcellulose, and DEAE-Sephadex, starch, β- or γ-cyclodextrin, preferably cholestyramine, colestipol, colesevelam, colestimide, sevelamer, DEAE-cellulose, and β- or γ-cyclodextrin, more preferably cholestyramine, colestipol, sevelamer, DEAE-cellulose, and β- or γ-cyclodextrin, most preferably cholestyramine, colestipol, and sevelamer.

In a preferred embodiment of the present invention, the bile acid sequestrant is cholestyramine. In a further preferred embodiment, the bile acid sequestrant is colestipol. In a additional embodiment the bile acid sequestrant is sevelamer.

Pharmaceutical compositions incorporating both a compound of a lipase inhibitor and a bile acid sequestrant are important embodiments of the present invention. Such pharmaceutical compositions comprise a therapeutically effective amount of each of the compounds. Each dosage unit can obtain the daily doses of both compounds or may contain a fraction of the daily dose, such as one-third of the doses. Alternatively, each dosage unit may contain the entire dose of one of the compounds, and a fraction of the dose of the other compound. In such case the patient would daily take one of the combination dosage units, and one or more units containing only the other compound.

Particularly, the above composition refer to compositions comprising a) about 5 to about 1000 mg lipase inhibitor and b) about 0.1 to about 20 g bile acid sequestrant. The compositions may comprise a pharmaceutically acceptable excipient, e.g. a diluent or carrier. The pharmaceutically acceptable excipient may be selected from the group consisting of fillers, e.g. sugars and/or sugar alcohols, e.g. lactose, sorbitol, mannitol, maltodextrin, etc.; surfactants, e.g. sodium lauryle sulfate, Brij 96 or Tween 80; disintegrants, e.g. sodium starch glycolate, maize starch or derivatives thereof; binder, e.g. povidone, crosspovidone, polyvinylalcohols, hydroxypropylmethylcellulose; lubricants, e.g. stearic acid or its salts; flowability enhancers, e.g. silicium dioxide; sweeteners, e.g. aspartame; and/or colorants, e.g. β-carotene.

A preferred composition may comprise a) about 5 to about 1000 mg lipase inhibitor; b) about 0.1 to about 20 g bile acid sequestrant; and optionally pharmaceutically acceptable excipients selected from the group of about 0.1 to about 10 g fillers, about 0.05 to about 3.0 g surfactant, about 0.05 to about 2.0 g disintegrant, about 0.02 to about 2.0 g binder, about 0.001 to about 1.0 g lubricant, about 0.1 to about 5.0 g flowability enhancer, about 0.01 to about 4.0 g sweetener, and about 0.001 to about 0.5 g colorant. The preferred lipase inhibitor is orlistat.

In particular, the invention refers to pharmaceutical compositions comprising orlistat, a pharmaceutically acceptable bile acid sequestrant in conjunction with a pharmaceutically acceptable excipient, e.g. a diluent or carrier, preferably to compositions wherein the pharmaceutically acceptable bile acid sequestrant is selected from as defined above. More preferably the compositions containing both a lipase inhibitor, e.g. orlistat and a bile acid sequestrant as described above may comprise 5 to 1000 mg lipase inhibitor, preferably about 10 to about 500 mg lipase inhibitor, more preferably about 20 to about 100 mg lipase inhibitor, e.g. orlistat. The preferred amounts for orlistat are about 10 to about 360 mg, preferably about 30 to about 120 mg and most preferably about 40 to about 80 mg.

The pharmaceutical compositions may contain about 0.1 to about 20 g bile acid sequestrant, preferably about 0.5 to about 10 g, and most preferably about 1 to about 5 g.

The invention also refers to a process for preparing a composition as described above, comprising mixing a lipase inhibitor or a pharmaceutically acceptable salt thereof with a bile acid sequestrant or a pharmaceutically acceptable salt thereof and one or more pharmaceutically acceptable excipient, e.g. a diluent and/or carrier.

Oral dosage forms are the preferred compositions for use in the present invention and these are the known pharmaceutical forms for such administration, for example tablets, capsules, bars, sachets, granules, syrups and aqueous or oily suspensions. The pharmaceutically acceptable excipients (diluents and carriers) are known in the pharmacist's art. Tablets may be formed form a mixture of the active compounds with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound with or without added excipients, may be prepared by known methods. The contents of the capsule may be formulated using known methods so as to give sustained release of the active compound. For example, the tablets and capsules may conveniently each contain the amounts of lipase inhibitor and bile acid sequestrant as described above.

Other dosage forms for oral administration include, for example, aqueous suspensions containing the active compounds in an aqueous medium in the presence of a non-toxic suspending agent such as sodium carboxymethylcellulose, and oily suspensions containing the active compounds in a suitable vegetable oil, for example arachis oil. The active compounds may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium.

In the compositions of the present invention the active compounds may, if desired, be associated with other compatible pharmacologically active ingredients. Optionally vitamin supplements may be administered with the compounds of the present invention.

Both compounds, the lipase inhibitor and the bile acid sequestrant may be administered simultaneously, separately or sequentially. Preferably, the compounds or compositions are administered during a meal or 1 to 2 hours before or after a meal. The amount of bile acid sequestrant to be administered will depend on a number of factors including the age of the patient, the severity of the condition and the past medical history of the patient and lies within the discretion of the administering physician. For example, β- and γ-cyclodextrin (starch derivatives), cholestyramine, colestipol (amine containing polymer) and diethylaminoethylcellulose (cellulose or dextran derivative) could be administered 0.1–20 g per day, preferably 1–10 g per day, starch, amylose and other bile acid sequestrants described above 1–20 g per day.

The invention also provides the use of the above combination of compounds in the manufacture of a medicament for the treatment and prevention of obesity. Additionally, it provides the combination and above compositions for use in the treatment and prevention of obesity.

The invention also refers to a kit for treatment of obesity, said kit comprising a first component which is a lipase inhibitor and b) a second component which is a bile acid sequestrant e.g. in an oral unit dosage forms, preferably comprising a) from 1 to 100 doses units of orlistat and b) from 1 to 100 doses units of a bile acid sequestrant.

Further, the present invention refers to the use of a composition as described above in the manufacture of medicaments useful for the treatment and prevention of obesity, e.g. the use of a lipase inhibitor in the manufacture of a medicament for the treatment and prevention of obesity in a patient who is also receiving treatment with a bile acid sequestrant or a pharmaceutically acceptable salt thereof.

In addition, the present invention refers to a method of treatment of obesity in a human in need of such treatment which comprises administration to the human of a therapeutically effective amount of a lipase inhibitor and a therapeutically effective amount of a bile acid sequestrant. Both compounds, the lipase inhibitor and the bile acid sequestrant may be administered simultaneously, separately or sequentially.

Accordingly, the present invention also relates to a lipase inhibitor and a bile acid sequestrant as defined above for the simultaneous, separate or sequential use for the treatment and prevention of obesity and to a combined preparation for simultaneous, separate or sequential use for the treatment and prevention of obesity.

The invention also refers to the use of a bile acid sequestrant as defined above in the manufacture of medicaments useful for the treatment and prevention of gastrointestinal side effects selected from the group of oily spotting, fatty/oily stools, fecal urgency, increased defecation and fecal incontinence. Further, the invention also refers to a method of treatment or prevention of gastrointestinal side effects selected from the group of oily spotting, fatty/oily stools, fecal urgency, increased defecation and fecal incontinence in a human in need of such treatment which comprises administration to the human of a therapeutically effective amount of of a bile salt sequestrant as defined above.

The invention will be better understood by reference to the following examples which illustrate but do not limit the invention described herein.

EXAMPLES

Example 1

Study A

Xenical was ingested t.i.d. by two middle aged healthy male volunteers on a normal average mixed diet. Both individuals frequently experienced one or more of the above mentioned unpleasant gastrointestinal side effects. After 4 weeks on Xenical they started to ingest in addition to Xenical b.i.d. cholestyramine containing sachets (4 g/meal) which were emptied into about 100 ml water, swirled and drunk during the meals. The side effects were immediately reduced in frequency and completely disappeared. After 2–4 weeks of combined intake together with Xenical, cholestyramine was discontinued. When treatment with Xenical alone was carried on the gastrointestinal adverse events reappeared.

Example 2

Study B

The anti-GI side effect potential of bile salt sequestrants was extended further in short-term studies in human volunteers. To precipitate the tendency for side effects in this model three meals (lunch, dinner, breakfast) are ingested together with Xenical and 120 mg orlistat in 10 g butter, each. The model is based on the idea that GI side effects following orlistat ingestion are precipitated by the formation of free oil. Free oil is oil, which will coalesce in the dietary fat emulsion passing down the GI tract and separate from the stool matrix. In this model the amount of oil which is separated from the stool matrix is determined after the production of stools.

It was demonstrated in human volunteers that after co-administration of cholestyramine and colestipol, respectively, the formation of free oil was dramatically reduced (cholestyramine: 44% of the respective control experiment without addition of cholestyramine) or nearly completely suppressed (colestipol: 6% of the respective control experiment without addition of colestipol). Total fat excretion remained unchanged.

Free oil formation following intake of 3x a high dose of orlistat with fatty meals and reduction by bile salt sequestrants (grams per test)

| Experiment | Control | Colestipol 4 g t.i.d. | Cholestyramin 4 g t.i.d. | % of control |
|---|---|---|---|---|
| 1 | 49 | | 9 | 18 |
| 2 | 35 | | 40 | 114 |
| 3 | 51 | | 4 | 8 |
| 4 | 10 | | 2 | 20 |
| 5 | 64 | | 25 | 39 |
| 6 | 46 | | 43 | 93 |
| 7 | 76 | | 3 | 4 |
| average | 47 ± 21 | | 18 ± 18 | 42 ± 44 |
| 1 | 11 | 0 | | 0 |
| 2 | 9 | 0 | | 0 |
| 3 | 51 | 0 | | 0 |
| 4 | 34 | 0 | | 0 |
| s | 64 | 8 | | 13 |
| 6 | 71 | 18 | | 25 |
| average | 40 ± 26 | 4 ± 7 | | 6 ± 11 |

Example 3

Orlistat Pharmaceutical Compositions

A)

| Ingredient | Quantity mg/Capsule |
|---|---|
| orlistat | 120.00 |
| microcrystalline cellulose (AVICEL PH-101) | 93.60 |
| sodium starch glycolate (PRIMOJEL) | 7.20 |
| sodium lauryl sulfate | 7.20 |
| polyvinylpyrrolidone (Povidone (K-30)) | 12.00 |
| purified Water* | — |
| talc | 0.24 |
| Total | 240.24 mg |

*Removed during processing

Procedure

Blend orlistat, microcrystalline cellulose, and sodium starch glycolate in a suitable mixer.
Granulate with a solution of polyvinylpyrrolidone and sodium lauryl sulfate in purified water.
Pass the granulation through an extruder and pass the extrudate through a spheronizer to form pellets.
Dry the pellets at 30° C.
Add talc and mix.
Fill into hard gelatin capsules.

B)

| Ingredient | Quantity mg/Capsule |
|---|---|
| orlistat | 60 |
| microcrystalline cellulose | 46.8 |
| sodium starch glycolate | 3.6 |
| sodium lauryl sulfate | 3.6 |
| polyvinylpyrrolidone | 6.0 |
| purified water* | — |
| talc | 0.12 |
| Total | 120.12 mg |

*Removed during processing.

Procedure

Blend orlistat, microcrystalline cellulose, and sodium starch glycolate in a suitable mixer.
Granulate with solution of polyvinylpyrrolidone and sodium lauryl sulfate in purified water.
Pass the granulation through an extruder and pass the extrudate through a spheronizer to form pellets.
Dry the pellets at 30° C.
Add talc and mix.
Fill into hard gelatin capsules.

C)

| Ingredient | Quantity mg/Capsule | |
|---|---|---|
| orlistat | 60 | 120 |
| lactose | 40 | 80 |
| microcrystalline cellulose | 60 | 120 |
| sodium lauryl sulfate | 5.7 | 11.4 |
| sodium starch glycolate | 20 | 40 |
| polyvinylpyrrolidone | 10 | 20 |
| purified water* | — | — |
| talc | 0.2 | 0.4 |
| Total | 195.9 mg | 391.8 mg |

*Removed during processing.

Procedure

Blend orlistat, lactose, microcrystalline cellulose and sodium starch glycolate in a suitable mixer.
Granulate with a solution of polyvinylpyrrolidone and sodium lauryl sulfate in purified water.
Pass the granulation through an extruder, and pass the extrudate through a spheronizer to form pellets.
Dry the pellets at 30° C.
Add talc and mix.
Fill into hard gelatin capsules.

Example 4

Bile Acid Sequestrant Pharmaceutical Compositions

| Ingredient | Quantity mg/Capsule |
|---|---|
| cholestyramine | 4 g |
| silicium Dioxide | 0.495 g |
| aspartame | 0.05 g |
| β-carotene | 0.001 g |
| purified water* | — |
| Total | 4.5 g |

*Removed during processing

Procedure

Blend colestyramine, and silicium dioxide in a suitable mixer.
Granulate with a solution /colloidal suspension of aspartame and beta-carotene in purified water.
Pass the granulation through an sieve.
Dry the granules at 60° C.
Pass the dry granulation through an sieve
Fill into sachets.

Example 5

Bile Acid Sequestrant Pharmaceutical Compositions

| Ingredient | Quantity mg/Capsule |
|---|---|
| cholestyramine | 4 g |
| silicium dioxide | 0.5 g |
| saccharose | 3 g |
| β-carotene | 0.001 g |
| purified water* | — |
| total | 7.5 g |

*Removed during processing

Procedure

Blend colestyramine, silicium dioxide, and saccharose in a suitable mixer.
Granulate with a solution/colloidal suspension of aspartame and beta-carotene in purified water.
Pass the granulation through an sieve.
Dry the granules at 60° C.
Pass the dry granulation through an sieve
Fill into sachets.

Example 6

Bile Acid Sequestrant Pharmaceutical Compositions

| Ingredient | Quantity mg/Capsule |
|---|---|
| cholestyramine | 4 g |
| aspartame | 0.5 g |
| β-carotene | 0.001 g |
| purified water* | — |
| Total | 4.05 g |

*Removed during processing

Procedure

Fill colestyramine in a suitable mixer.
Granulate with a solution /colloidal suspension of aspartame and beta-carotene in purified water.
Pass the granulation through an sieve.
Dry the granules at 60° C.
Pass the dry granulation through an sieve
Fill into sachets.

Example 7

Orlistat/Bile Acid Sequestrant Pharmaceutical Compositions

| Ingredient | Quantity mg/Capsule |
|---|---|
| orlistat | 120 mg |
| maltodextrinum | 740 mg |
| cholestyramine | 4000 mg |
| aspartame | 440 mg |
| purified water* | — |
| total | 5.3 g |

*Removed during processing

Procedure

Melt orlistat in a mixer and add maltodextrin.
Mix until solidification at room temperature (first part)
Add cholestyramine and mix
Granulate with a solution/colloidal suspension of aspartame in purified water.
Pass the granulation through an sieve.
Dry the granules at 60° C.
Pass the dry granulation through an sieve (second part)
Blend both parts in a mixer
Fill into sachets.

Example 8

Orlistat/Bile Acid Sequestrant Pharmaceutical Compositions

| Ingredient | Quantity mg/Capsule |
|---|---|
| orlistat | 120 mg |
| microcrystalline cellulose | 240 mg |
| sodium starch glycolate | 60 mg |
| sodium lauryl sulfate | 30 mg |
| crospovidone | 50 mg |
| cholestyramine | 4000 mg |
| aspartame | 200 mg |
| purified water* | — |
| total | 5.2 g |

*Removed during processing

Procedure

Blend cholestyramine, orlistat, microcristalline cellulose (Avicel), sodium starch glycolate and crospovidone in a suitable mixer.
Granulate with a solution/colloidal suspension of sodium lauryl sulfate, aspartame in purified water.
Pass the granulation through an sieve.
Dry the granules at 30° C.
Pass the dry granulation through a sieve
Fill into sachets.

Example 9

Orlistat/Bile Acid Sequestrant Pharmaceutical Compositions

| Ingredient | Quantity mg/Capsule |
|---|---|
| orlistat | 120 mg |
| maltodextrinum | 740 mg |
| colestipol | 4000 mg |
| aspartame | 440 mg |
| purified water* | — |
| total | 5.3 g |

*Removed during processing

Procedure

Melt orlistat in a mixer and add maltodextrin.
Mix until solidification at room temperature (first part)
Add colestipol and mix.
Granulate with a solution/colloidal suspension of aspartame in purified water.
Pass the granulation through an sieve.
Dry the granules at 60° C.
Pass the dry granulation through an sieve (second part)
Blend both parts in a mixer
Fill into sachets.

Example 10

Orlistat/Bile Acid Sequestrant Pharmaceutical Compositions

| Ingredient | Quantity mg/Capsule |
|---|---|
| orlistat | 120 mg |
| microcrystalline cellulose | 240 mg |
| sodium starch glycolate | 60 mg |
| sodium lauryl sulfate | 30 mg |
| crospovidone | 50 mg |
| colestipol | 4000 mg |
| aspartame | 200 mg |
| purified water* | — |
| total | 5.2 g |

*Removed during processing

Procedure

Blend colestipol, orlistat, microcristalline cellulose (Avicel), sodium starch glycolate and crospovidone in a suitable mixer.
Granulate with a solution/colloidal suspension of sodium lauryl sulfate, aspartame in purified water.
Pass the granulation through an sieve.
Dry the granules at 30° C.
Pass the dry granulation through a sieve
Fill into sachets.

Upon reading this specification, various alternative embodiments will become obvious to the skilled artisan. These variations are to be considered within the scope and spirit of the subject invention, which is only to be limited by the claims that follow and their equivalents.

What is claimed is:

1. A method of reducing the gastrointestinal side effects associated with orlistat treatment, which comprises administering to a patient being treated with orlistat an amount of a bile salt sequestrant selected from the group consisting of cholestyramine, colestipol, colestimide, colesevelam, sevelamer, DEAE-cellulose, β-cyclodextrin, γ-cyclodextrin, guanidinoethylcellulose, and DEAE-Sephadex, effective to reduce the side effects associated with the orlistat treatment.

* * * * *